United States Patent [19]

Parkinson

[11] Patent Number: 4,518,614

[45] Date of Patent: May 21, 1985

[54] COSMETIC PREPARATION

[75] Inventor: Richard W. Parkinson, Orem, Utah

[73] Assignee: Redken Laboratories, Inc., Canoga Park, Calif.

[21] Appl. No.: 546,654

[22] Filed: Oct. 28, 1983

Related U.S. Application Data

[63] Continuation-in-part of Ser. No. 439,113, Nov. 4, 1982, abandoned.

[51] Int. Cl.$^3$ .................. A61K 47/00; A61K 31/365
[52] U.S. Cl. ...................................... 514/2; 514/468; 514/474; 514/564; 514/588
[58] Field of Search ............................... 424/359, 365

[56] References Cited

U.S. PATENT DOCUMENTS

| | | | |
|---|---|---|---|
| 1,332,190 | 2/1920 | Hull | 424/358 |
| 3,038,794 | 6/1962 | Geary et al. | 549/297 X |
| 3,970,759 | 7/1976 | Frankenfeld | 424/70 |
| 4,154,823 | 5/1979 | Schutt | 424/195 |

FOREIGN PATENT DOCUMENTS

| | | | |
|---|---|---|---|
| 844549 | 8/1960 | United Kingdom | 549/297 |
| 910004 | 11/1962 | United Kingdom | 424/359 |
| 1228888 | 4/1971 | United Kingdom | 549/297 |

OTHER PUBLICATIONS

Merck Index, 1976, pp. 569 & 570.
The Cosmetic Formulary, Bennett, 8/1941, pp. 2 to 15, 36 and 37.

*Primary Examiner*—Dale R. Ore
*Attorney, Agent, or Firm*—Terry M. Crellin

[57] ABSTRACT

A cosmetic preparation is disclosed which is effective in moisturizing and softening skin, improving texture and feel of skin, and diminishing superficial and deep wrinkles in skin. The preparation comprises gibberellic acid and lysine as active ingredients. The preparation can contain as additional active ingredients gliadin, ascorbic acid and urea.

6 Claims, No Drawings

COSMETIC PREPARATION

This application is a continuation-in-part of application Ser. No. 439,113 filed Nov. 4, 1982, now abandoned.

FIELD OF THE INVENTION

The present invention relates to cosmetic preparations and in particular to cremes, lotions and liquids for moisturizing the skin.

BACKGROUND ART

Many cosmetic preparations of the creme, lotion, and liquid type are currently in use. There is considerable variation in the specific formulations making up the oil and water phases of such preparations. Mineral oils, animal oils and vegetable oils have all been used in cosmetic cremes and lotions of the emulsion type. In addition to such oils, other emolients and surface active agents have been incorporated in the emulsions, including stearates, such as potassium stearate, glycol stearate, sodium stearate, PEG 40 stearate and glyceryl stearate; laurates, such as sodium laurate and potassium laurate; alcohols, such as cetyl alcohol and lanolin alcohol; triethanolamine; myristates, such as isopropyl myristate, sodium myristate and potassium myristate; cetyl palmitate; cholesterol; stearic acid; and sorbitan sesquioleate. Stabilizers, such as methyl paraben and propyl paraben, are commonly incorporated in the cosmetic preparations.

DISCLOSURE OF INVENTION

A principal object of the present invention is to provide an improved cosmetic preparation of either the liquid or of the emulsion type wherein the improved preparation is most effective in moisturizing the epidermis, softening the skin, improving the texture and feel of the skin and diminishing superficial and deep wrinkles in the skin.

The above objective is achieved in accordance with the present invention by providing a cosmetic preparation of the creme, lotion, or liquid variety which has incorporated therein from about 0.1% up to about 1% gibberellic acid and from about 0% up to 5% lysine. Advantageously, the lysine utilized in the preparation is L-lysine which is a natural occurring form of lysine. However, the dextro isomer can be used as well as analog of lysine, such as hydroxy lysine. The improved preparation may also contain from about 0.01% to 5% gliadin, from about 0.005% to 1% ascorbic acid, from about 0.01% to 5% urea and up to 1% calcium.

It has been found that the performance of the liquid water base preparations and the water-oil emulsion type preparation, can be substantially and markedly enhanced with respect to moisturizing the epidermis, softening the skin, improving the texture and feel of the skin and in diminishing superficial and deep wrinkles in the skin by incorporating the above mentioned ingredients into the cosmetic preparations.

DESCRIPTION OF PREFERRED EMBODIMENTS

Cosmetic preparations, either cremes, lotions or liquids can be prepared in accordance with the present invention from numerous cosmetic base ingredients which are well known in prior art. Such bases may comprise emulsions containing various emollient ingrdients. Lanolin or other oils from the group consisting of animal oils, vegetable oils and mineral oils are emulsified with water as is well known in the art. In addition to the oils, other emollients and surface active agents such as those mentioned hereinbefore can be incorporated in the emulsions as is also well known in the art. Stabilizers and preservatives can be included within the cosmetic preparation as is also well known in the art.

The essence of the present invention is not within the composition of the base per se, and any of extremely many base formulations or compositions of the water or emulsion type currently used in cosmetic skin preparations can be employed. The essence of the present invention is in the incorporation of specific ingredients within the creme, lotion, or liquid preparation which substantially and markedly enhance the performance of the cosmetic preparation in moisturizing the epidermis, softening the skin, improving the texture and feel of the skin and in diminishing superficial and deep wrinkles in the skin. There has heretofore, to the best of my knowledge, been no suggestions of the use of the combination of specific active ingredients as disclosed herein in a cosmetic preparation.

In accordance with the invention, a cosmetic preparation of exceptional performance is achieved. The cosmetic preparation comprises a creme, lotion or liquid base which has incorporated therein about 0.01% up to about 1% gibberellic acid and from about 0% up to about 5% lysine. The improved cosmetic preparation may also contain, in addition to the gibberellic acid and lysine, up to about 5% gliadin, up to about 1% ascorbic acid and up to 5% urea. Preferable concentrations of the latter ingredients when used in the cosmetic preparation are from about 0.03% to 1% gliadin, from about 0.01% to 0.05% L-ascorbic acid and from about 0.03% to 1% urea. The improved cosmetic preparation may also contain, in addition to the above-mentioned ingredients up to about 1% calcium. All percentages given throughout the specification and claims are by weight.

As an aid to practicing the present invention, a specific formulation of a preferred embodiment of a cosmetic creme in accordance with the invention is as follows:

| Component | Parts By Weight |
| --- | --- |
| Water | 85.0 |
| Safflower Oil | 6.0 |
| Mineral Oil | 4.5 |
| Ceraphyl 847 | 4.0 |
| Sorbitol (70% aqueous solution) | 3.0 |
| Stearic Acid | 2.5 |
| Lysine | 2.0 |
| Acetylated Lanolin Alcohol | 1.5 |
| Cetyl Alcohol | 1.2 |
| Acetylated Lanolin | 1.0 |
| Pur-Cellin Oil | 1.0 |
| Brij 700 | 1.0 |
| Triethanolamine | 1.0 |
| Glyceryl Monostearate | 0.9 |
| Urea | 0.5 |
| Methyl Paraben | 0.2 |
| Dawcil-200 | 0.15 |
| Propyl Paraben | 0.05 |
| Gliadin | 0.04 |
| Ascorbic Acid | 0.01 |
| Gibberellic Acid | 0.05 |

Using the cosmetic creme of the above formula, comparative tests were made in which 50 women between the ages of 24 and 68, all of whom were in good health with no relevant skin diseases, tested the creme of this invention in comparison to four commercially available cosmetic skin cremes. The women were divided into five groups of ten subjects. In four of the groups, each women was given a container of creme in accordance with this invention and a container of a commercially available skin creme. In the fifth group, the women were given a container of creme in accordance with the invention and a container of the creme base of the test product of this invention, i.e., the same creme but lacking the lysine, urea, gliadin, ascorbic acid and the gibberellic acid. The only markings on the containers given the women were instructions to apply the creme from the respective containers to one side of their faces with the creme in the other container being applied to the other side of their faces. All subjects were assessed after one month. Almost unanimously, the women reported a substantial improvement in visual appearance of the side of their faces to which the creme of this invention had been applied in comparison to the side to which the commercially available skin cremes and the creme base had been applied. A majority of the test subjects also reported a substantial improvement in the tactile condition of the side of their faces to which the creme of this invention had been applied in comparison to the side to which the commercially available skin cremes and the creme base had been applied. The subjects, when asked to select which creme they preferred, selected virtually unanimously the product of this invention.

Although preferred embodiments of the invention have been disclosed, it is to be understood that various changes and modifications can be made without departing from the subject matter coming within the scope of the following claims, which subject matter I regard as my invention.

I claim:

1. In a cosmetic skin composition comprising a creme, lotion, emulsion or liquid water base preparation wherein the improvement comprises from about 0.01% to 1% by weight gibberellic acid and from about 0.1% to 5% by weight lysine to soften the skin, improve the texture of the skin, moisturize the epidermis and diminish wrinkles in the skin.

2. The composition in accordance with claim 1, wherein the improved cosmetic skin composition further contains from about 0.01% to 5% by weight gliadin, from about 0.005% to 1% by weight ascorbic acid and from about 0.01% to 5% urea by weight.

3. The composition in accordance with claim 1, wherein the improved cosmetic skin composition comprises an emulsion containing water; at least one oil selected from the group consisting of mineral oil, vegetable oil and animal oil; and at least one emolient selected from the group consisting of potassium stearate, sodium stearate, cholesterol cetyl palmitate, sodium laurate, potassium laurate, sodium myristate, potassium myristate, stearic acid, glycerin cetyl alcohol, PEG 40 stearate, sorbitan sesquioleate, lanolin alcohol, pentasodium penetate, glycol stearate, triethanolamine, glyceryl stearate, isopropyl myristate, sorbitol, acetylated lanolin alcohol and acetylated lanolin.

4. A composition in accordance with claim 3, wherein the improved cosmetic skin composition further includes a compound selected from the group consisting of methyl paraben, propyl paraben and mixtures thereof.

5. A method for treating the skin to soften the skin, improve texture of the skin, moisturize the epidermis and diminish wrinkles in the skin, said method comprising topically applying an effective amount of a cosmetic skin composition to the skin, wherein the cosmetic skin composition comprises a creme, lotion, emulsion or liquid water base preparation, and said cosmetic skin composition containing from about 0.01% to 1% by weight gibberellic acid and from 0% up to about 5% by weight lysine.

6. A method in accordance with claim 5, wherein said cosmetic skin composition contains from about 0.1% to 5% by weight lysine.

* * * * *